United States Patent [19]

Brown

[11] 4,013,641
[45] Mar. 22, 1977

[54] INDOLOBENZOXAZEPINES
[75] Inventor: Richard E. Brown, East Hanover, N.J.
[73] Assignee: Xerox Corporation, Stamford, Conn.
[22] Filed: Oct. 8, 1975
[21] Appl. No.: 620,734
[52] U.S. Cl. .................... 260/239.3 P; 260/243 B; 260/247.5 FP; 260/268 PC; 260/293.58; 260/326.13 R; 260/326.14 R; 260/326.5 B; 260/248.57; 424/246; 424/250; 424/267; 424/274
[51] Int. Cl.$^2$ ....................................... C07D 498/04
[58] Field of Search ................ 260/239.3 P, 326.5, 260/243, 268, 293.58, 326.15, 247.5, 243 B, 247.5 FP, 268 PC, 326.5 B

*Primary Examiner*—G. Thomas Todd
*Attorney, Agent, or Firm*—James J. Ralabate; James P. O'Sullivan; John E. Crowe

[57] ABSTRACT

This invention relates to substituted indolobenzoxazepines which act as central nervous system depressants and as such are useful as tranquillizers.

15 Claims, No Drawings

INDOLOBENZOXAZEPINES

This invention relates to substituted indolobenzoxazepines of the following general formula:

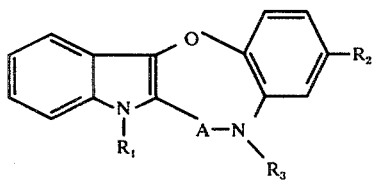

In this formula, $R_1$ may be hydrogen, lower alkyl of 1 to 6 carbon atoms or an aralkyl group of 1 to 6 carbon atoms in the chain; $R_2$ may be hydrogen, a halogen atom such as fluorine or chlorine, lower alkyl of 1 to 6 carbon atoms or a trifluoromethyl group. "A" may be a methylene group or a carbonyl group. $R_3$ may be hydrogen, lower alkyl of 1 to 6 carbon atoms, an aralkyl group of 1 to 6 carbon atoms in the chain, or an ω-aminoalkyl group of the formula

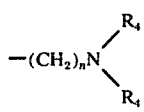

in which $n$ may be 2 to 4 and $R_4$ may be hydrogen, lower alkyl of 1 to 6 carbon atoms or, taken together with the N atom form a heterocyclic ring of the formula

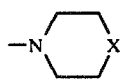

wherein X may be oxygen, sulfur, —$CH_2CH_2$—; a bond connecting the adjacent carbon atoms or CH-$R_5$ or N-$R_5$ wherein $R_5$ may be hydrogen or lower alkyl of 1 to 6 carbon atoms.

The products of this invention may be prepared according to the following reaction sequence starting with an ester of indoxylic acid, II:

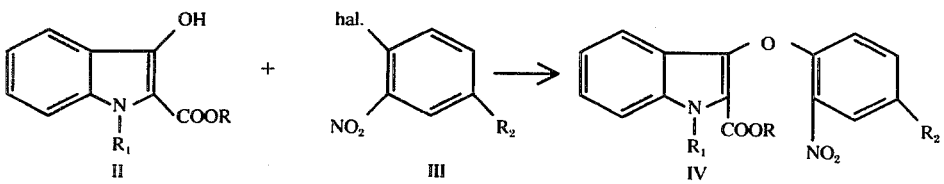

In structure II, R is a lower alkyl group of 1 to 6 carbon atoms and $R_1$ is as defined for I. These starting materials are known and were prepared according to methods described in the literature.

In the first step, the indoxylate ester is alkylated with an appropriately substituted o-halonitrobenzene of structure III to give an intermediate according to structure IV. In structure III, hal. refers to halogen and may be fluoride, chlorine, bromine or iodine. $R_2$ is as defined for structure I. This alkylation is carried out in a solvent such as a lower alcohol, THF, or, preferably, DMF in the presence of a weak base such as potassium carbonate.

In the second step, the nitro group of intermediate IV is reduced to give an amino group, as shown in structure V:

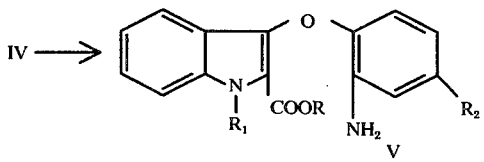

This reduction can be done catalytically in a solvent such as ethanol and using a catalyst such as platinum oxide, palladium on carbon or Raney Nickel, or it may be done chemically in a solvent such as ethanol using a metal such as iron fillings or zinc dust in the presence of an acid such as hydrochloric or acetic.

In the third step, the amino ester of structure V is hydrolyzed to give the amino acid of structure VI:

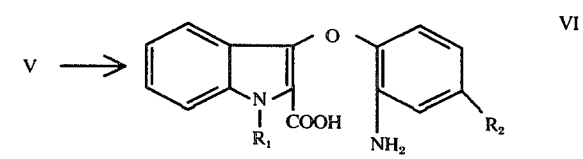

This hydrolysis is best carried out in an aqueous-alcoholic solvent system using an alkali metal hydroxide such as sodium or potassium hydroxide.

Alternatively, the order of sequence of the reduction and hydrolysis steps may be reversed so that intermediate IV is first hydrolyzed to afford a nitro acid of structure VII which is subsequently reduced to give VI.

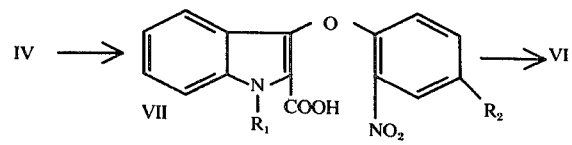

In the fourth step, ring closure of aminoacid VI to lactam VIII is carried out in a solvent such as ethanol or, preferably, THF, using an amide forming reagent such as dicyclohexylcarbodiimide, or, preferably, ethyl 1,2-dihydro-2-ethoxy-1-quinoline carboxylate.

VI → 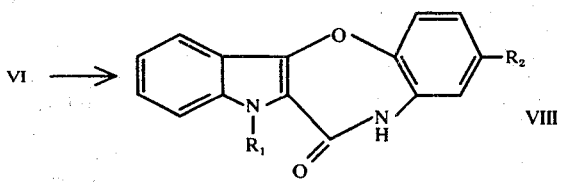 VIII

In the fifth step, lactam VIII is alkylated with an appropriately substituted halide, $R_3$ hal., to give a product of structure IX. The halides for this alkylation are selected from the group consisting of halides of lower alkanes of 1 to 6 carbon atoms, aralkyl halides containing 1 to 6 carbon atoms in the chain, or ω-aminoalkyl halides of the formula:

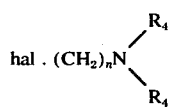

in which hal., n and $R_4$ are as previously defined.

The alkylation is best carried out in polar aprotic solvents such as DMF or DMSO using a strong base such as sodium or potassium hydride or amide as the catalyst.

VIII → 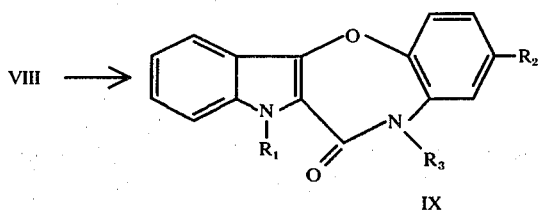

IX

In the final step, the compound of structure IX is reduced to afford a compound according to structure X. This reduction is best carried out with a complex hydride reagent such as lithium aluminum hydride in a solvent such as ether or THF.

IX → 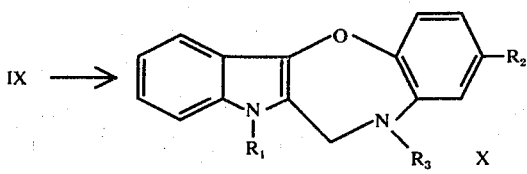 X

In order to prepare products in which $R_1$ is other than hydrogen, two methods may be used. In the first method, an $R_1$ substituted indoxylic ester is employed in step 1. Such starting materials may be synthesized according to the procedure exemplified in example 14. In the second method, an alkylation step may be carried out on structure IV wherein $R_1 =$ H. This alkylation is best carried out using a polar aprotic solvent such as THF, DMF or DMSO and a strong base such as sodium hydride or potassium amide as solvent. Among the alkylating agents which may be used are halides or alkanes of 1 to 6 carbon atoms, or aralkyl halides of 1 to 6 carbon atoms in the chain.

In order for a more thorough understanding of the subject matter of this application, the following examples are given:

EXAMPLE 1

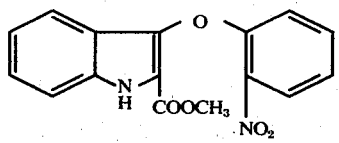

METHYL-3-[O-NITROPHENOXY]-INDOLE-2-carboxylate

A mixture of 5.73g (0.03 mole) of methyl indoxylate, 4.23g (0.03 mole) of o-fluoronitrobenzene, 4.14g (0.03 mole) of potassium carbonate and 50ml of DMF was heated with stirring for 6 hours on the steam bath.

The mixture was cooled, poured into water and filtered to give 6.7g of crude product. Recrystallization from acetonitrile gave analytical material, mp. 201°–2°.

Anal. Calcd. for $C_{16}H_{12}N_2O_5$: C, 61.54; H, 3.87; N, 8.97. Found: C, 61.39; N, 3.92; N, 8.45.

EXAMPLE 2

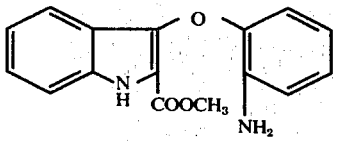

METHYL-3-[O-AMINOPHENOXY]-INDOLE-2-CARBOXYLATE

A mixture of 3.12g of methyl-3-[o-nitrophenoxy]-indole-2-carboxylate, 10g of 40 mesh iron filings, 5ml of 5% aqueous acetic acid and 300ml of ethanol was refluxed with stirring for 3 hours. The mixture was filtered and concentrated to a solid. Recrystallization from ethanol gave analytical material, mp. 183°–4°.

Anal. Calcd. for $C_{16}H_{14}N_2O_3$: C, 68.08; H, 5.00; N, 9.92. Found: C, 67.88; H, 5.19; N, 9.93.

EXAMPLE 3

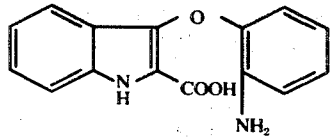

3-[O-AMINOPHENOXY]-INDOLE-2-CARBOXYLIC acid 1.6g of methyl-3-[o-aminophenoxy]-indole-2-carboxylate was dissolved in 10ml each of ethanol and water and refluxed for 10 min. The clear solution was acidified with acetic acid. The white precipitate was filtered and recrystallized from acetonitrile to give analytical material, mp. 217°–18°.

Anal. Calcd. for $C_{15}H_{12}N_2O_3$: C, 67.15; H, 4.51; N, 10.44. Found: C, 66.94; H, 4.59; N, 10.47.

EXAMPLE 4

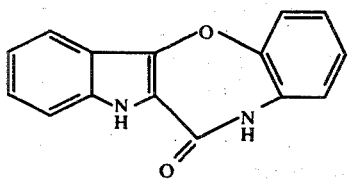

7H-INDOLO[3,2-B][1,5]BENZOXAZEPINE-6(5H)-ONE

A solution of 1.5g of 3-[o-aminophenoxy]-indole-2-carboxylic acid in 50ml of THF was treated with 1.48g of EEDQ and the clear solution left 18 hours at ambient temperature. The THF was removed by distillation, and the residue was rubbed with 2N HCl to give a yellow solid. Recrystallization from ethanol gave analytical material, mp. 233°–4°.

Anal. Calcd. for $C_{15}H_{10}N_2O_2$: C, 71.97; H, 4.03; N, 11.20. Found: C, 71.96; H, 4.02; N, 11.21.

EXAMPLE 5

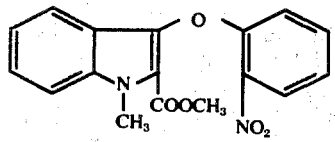

METHYL-3-[O-NITROPHENOXY]-1-METHYL-INDOLE2-CARBOXYLATE 6.73g (0.16 mole) of 57% sodium hydride in mineral oil was washed with hexane and suspended in 500ml of THF. To this was added 43.4g (0.139 mole) of methyl-3-[o-nitrophenoxy]-indole-2-carboxylate. The mixture was stirred at reflux for 1 hour, then 42.6g (.3 mole) of methyl iodide was added and reflux continued for 3 hour. Water (5ml) was added, the THF removed by distillation and the gummy residue recrystallized from isopropanol to give analytical material as yellow needles, mp. 119°–21°.

Anal. Calcd. for $C_{17}H_{14}N_2O_5$: C, 62.57; H, 4.32; N, 8.59. Found: C, 62.68; H, 4.38; N, 8.72.

EXAMPLE 6

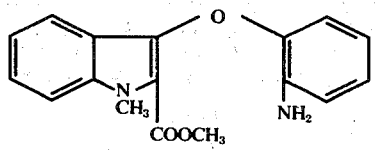

METHYL-3[O-AMINOPHENOXY-1-METHYL-INDOLE-2-CARBOXYLATE

In the same was as described in example 2, methyl-3-[o-nitrophenoxy]-1-methyl indole-2-carboxylate was reduced and the crude product recrystallized from methanol to give analytical material, mp. 103°–5°.

Anal. Calcd. for $C_{17}H_{16}N_2O_3$: C, 68.90; H, 5.44; N, 9.45. Found: C, 68.75; H, 5.60; N, 9.58.

EXAMPLE 7

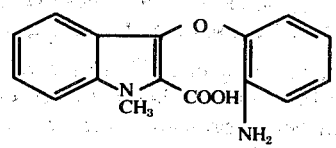

3-[O-AMINOPHENOXY]-1-METHYL-INDOLE2-CARBOXYLIC ACID

In the same way as described in example 3, methyl-3-[o-aminophenoxy]-1-methylindole-2-carboxylate was hydrolyzed and the crude product recrystallized from ethanol to give analytical material, mp. 193°–4°.

Anal. Calcd. for $C_{16}H_{14}N_2O_3$: C, 68.07; H, 5.00; N, 9.92. Found: C, 67.94; H, 5.22; N, 9.97.

EXAMPLE 8

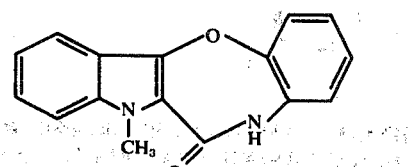

7-METHYL-7H-INDOLE3,2-B][1,5]BENZOXAZEPINE-6(5H)-ONE

In the same way as described in example 4, 3-[o-aminophenoxy]-1-methyl-indole-2-carboxylic acid was cyclized with EEDQ. Analytical material was obtained by recrystallization from acetonitrile, mp. 247°–8°.

Anal. Calcd. for $C_{16}H_{12}N_2O_2$: C, 72.71; H, 4.58; N, 10.60. Found: C, 72.69; H, 4.66; N, 10.85.

EXAMPLE 9

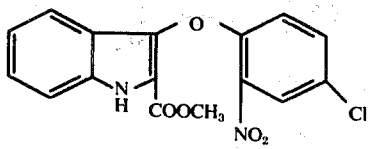

METHYL-3-[2-NITRO-4-CHLOROPHENOXY]-INDOLE-2CARBOXYLATE

In the same way as described in example 1, methylindoxylate and 2,5-dichloronitrobenzene was reacted. Recrystallization from ethanol gave analytical material, mp. 171°-2°.

Anal. Calcd. for $C_{16}H_{11}N_2O_5Cl$: C, 55.43; H, 3.20; N, 8.08; Cl, 10.72. Found: C, 55.24; H, 3.48; N, 7.88; Cl, 10.50.

EXAMPLE 10

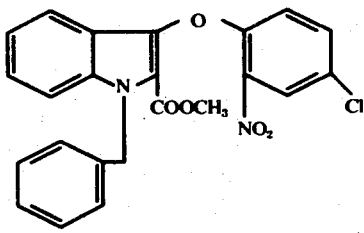

METHYL-3-[2-NITRO-4-CHLOROPHENOXY]-1-BENZYL-INDOLE-2carboxylate

In the same way as described in example 5, methyl-3-[2-nitro-4-chlorophenoxy]-indole-2-carboxylate was alkylated with benzyl bromide. Analytical material was obtained by recrytallization from ethanol, mp. 120°-1°.

Anal. Calcd. for $C_{23}H_{17}N_2O_5Cl$: C, 63.24; H, 3.92; N, 6.41; Cl, 8.12. Found: C, 63.15; H, 3.97; N, 6.39; Cl, 8.30.

EXAMPLE 11

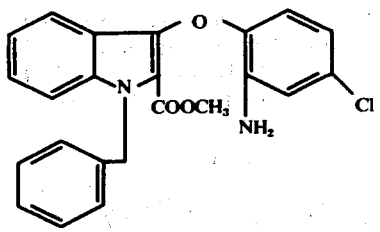

METHYL-3-[2-AMINO-4-CHLOROPHENOXY]-1-BENZYL-INDOLE-2-CARBOXYLATE

In the same way as described in example 2, methyl-3-[2-nitro-4-chlorophenoxy]-1-benzyl-indole-2-carboxylate was reduced and the crude product recrystallized from ethanol to give analytical material, mp. 121°-3°.

Anal. Calcd. for $C_{23}H_{19}N_2O_3Cl$: C, 67.90; H, 4.71; N, 6.88; Cl, 8.71. Found: C, 67.85; H, 4.80; N, 6.76; Cl, 8.96.

EXAMPLE 12

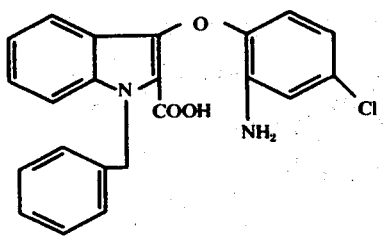

3-[2-AMINO-4-CHLOROPHENOXY]-1-BENZYL-INDOLE-2-CARBOXYLIC ACID

In the same was as described in example 3, methyl-3-[2-amino-4-chlorophenoxy]-1-benzyl-indole-2-carboxylate was hydrolyzed an the crude product recrystallized from 95% ethanol to give analytical material, mp. 218°-19°.

Anal. Calcd. for $C_{22}H_{17}N_2O_3Cl$: C, 67.26; H, 4.36; N, 7.13; Cl, 9.02. Found: C, 67.17; H, 4.40; N, 7.05; Cl, 9.19.

EXAMPLE 13

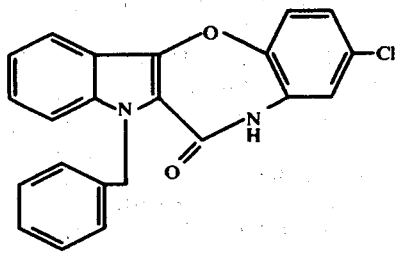

3-CHLORO-7-BENZYL-7H-INDOLO[3,2-B][1,5]benzoxazepine-6(5H)-ONE

In the same way as described in example 4, 3-[2-amino-4-chlorophenoxy]-1-benzyl-indole-2-carboxylic acid was cyclized, and the crude product was recrystallized from aqueous THF to give analytical material, mp. 259°-61°.

Anal. Calcd. for $C_{22}H_{15}N_2O_2Cl$: C, 70.50; H, 4.03; N, 7.47; Cl, 9.46. Found: C, 70.48; H, 4.12; N, 7.20; Cl, 9.59.

EXAMPLE 14

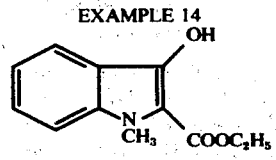

ETHYL-N-METHYL INDOXYLATE

A mixture of 38.8g (0.2 mole) of ethyl chloromalonate and 44g (0.41 mole) of N-methylaniline was heated on the steam bath for 72 hours. After cooling, the mixture was diluted with 500ml of methylene chloride and unreacted N-methylaniline extracted with 4N HCl. The methylene chloride layer was dried and concentrated to 49g of oil. This was diluted with 49ml of hexamethylphosphoramide, and the mixture was heated rapidly to boiling (bath temp. 245°). Reflux was continued for 20 minutes, the mixture cooled rapidly and poured into 400ml of 4N HCl. The crude solid product was filtered and recrystallized from isopropanol to give crystals, mp. 95°-6°.

EXAMPLE 15

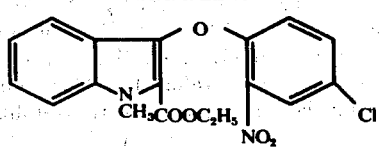

ETHYL-3-[2-NITRO-4-CHLOROPHENOXY]-1-METHYL-INDOLE-2-CARBOXYLATE

In the same was as described in example 1, ethyl-N-methyl indoxylate was alkylated with 2,5-dichloro nitrobenzene and the crude product recrystallized from isopropanol to give analytical material, mp. 133°–4°.

Anal. Calcd. for $C_{18}H_{15}N_2O_5Cl$: C, 57.69; H, 4.03; N, 7.47; Cl, 9.46. Found: C, 57.97; H, 4.09; N, 7.47; Cl, 9.70.

EXAMPLE 16

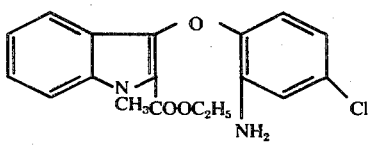

ETHYL-3-[2-AMINO-4-CHLOROPHENOXY]-1-METHYL-INDOLE-2-CARBOXYLATE.

In the same way as described in example 2, ethyl-3-[2-nitro-4-chlorophenoxy]-1-methyl-indole-2-carboxylate was reduced and the crude product recrystallized from ethanol, mp. 118°–20°.

Anal. Calcd. for $C_{18}H_{17}N_2O_3Cl$: C, 62.70; H, 4.97; N, 8.12; Cl, 10.28. Found: C, 62.82; H, 5.07; N, 8.05; Cl, 10.56.

EXAMPLE 17

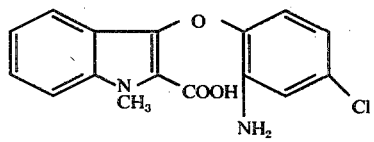

3-[2-AMINO-4-CHLOROPHENOXY]-1-METHYL-INDOLE-2-CARBOXYLIC ACID

In the same way as described in example 3, ethyl-3-[2-amino-4-chlorophenoxy]-1-methyl-indole-2-carboxylate was hydrolyzed and the crude product recrystallized from 95% ethanol to give analytical material, mp. 204°–6°.

Anal. Calcd. for $C_{16}H_{13}N_2O_3Cl$: C, 60.67; H, 4.14; N, 8.84; Cl, 11.19. Found: C, 60.70; H, 4.21; N, 8.90; Cl, 11.09.

EXAMPLE 18

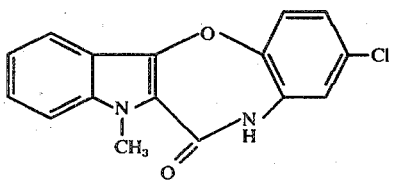

3-CHLORO-7-METHYL-7H-INDOLO[3,2-B][1,5]benzoxazepine-6(5H)-ONE.

In the same way as described in example 4, 3-[2-amino-4-chlorophenoxy]-1-methyl-indole-2-carboxylic acid was cyclized, and the crude product, insoluble in all solvents, was purified by digesting for 1 hour in hot THF and filtering while hot, mp. 306°–7°.

Anal. Calcd. for $C_{16}H_{11}N_2O_2Cl$: C, 64.33; H, 3.71; N, 9.38; Cl, 11.87. Found: C, 64.20; H, 3.73; N, 9.15; Cl, 12.40.

EXAMPLE 19

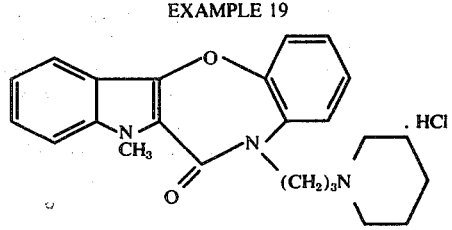

7-METHYL-5-(3-PIPERIDINOPROPYL)7H-INDOLO[3,2-B][1,5]BENZOXAZEPIN-6(5H)-ONE HYDROCHLORIDE

A mixture of 1.8g of 7-methyl-7H-indolo [3,2-b][1,5]benzoxazepin-6(5H)-one, 0.42g of 57% sodium hydridemineral oil dispersion and 10ml of THF was refluxed for 15 min. and then treated with 4.0g of 3-chloropropylpiperidine. The mixture was refluxed for 24 hrs., diluted with 2N HCl and extracted with ether. The aqueous layer was made basic with 5% NaOH and the oil extracted with ether. The ether phase was dried and treated with dry HCl to give a white solid. The solid was recrystallized from methanol-ether to give analytical material, mp. 205°–6°.

Anal. Calcd. for $C_{24}H_{27}N_3O_2.HCl$: C, 67.67; H, 6.63; N, 9.86; Cl, 8.32. Found: C, 67.56; H, 6.78; N, 9.72; Cl, 8.59.

EXAMPLE 20

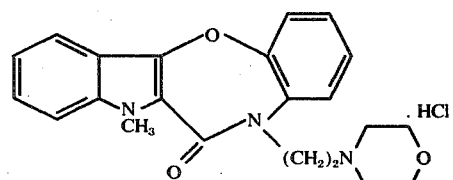

7-METHYL-5-(3-MORPHOLINOETHYL)-7H-INDOLO[3,2-B][1,5]BENZOXAZEPINE-6(5H)-ONE HYDROCHLORIDE

In the same way as described in example 19, 7-methyl-7H-indolo[3,2-b][1,5]benzoxazepine-6(5H)-one was alkylated with 2-(chloroethyl)morpholine and the crude hydrochloride recrystallized from ethanol to give analytical material, mp. 266°–8°.

Anal. Calcd. for $C_{22}H_{23}N_3O_3.HCl$: C, 63.84; H, 5.84; N, 10.15; Cl, 8.57. Found: C, 63.58; H, 5.86; N, 10.25; Cl, 8.49.

EXAMPLE 21

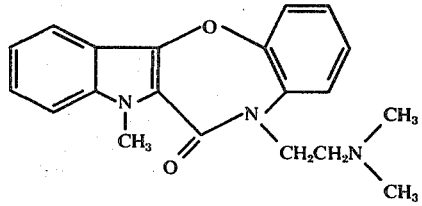

7-METHYL-5-[(2-DIMETHYLAMINO)ETHYL]-7H-INDOLO-[3,2-B][1,5]BENZOXAZEPINE-6(5H)-ONE

In the same way as described in example 19, 7-methyl-7H-indolo[3,2-b][1,5]benzoxazepine-6(5H)-one was alkylated with dimethylaminoethyl chloride, and the crude obtained by removal of the ether was recrystallized from methanol, mp. 119°–21°.

Anal. Calcd. for $C_{20}H_{21}N_3O_2$: C, 71.62; H, 6.31; N, 12.53. Found: C, 71.66; H, 6.40; N, 12.69.

EXAMPLE 22

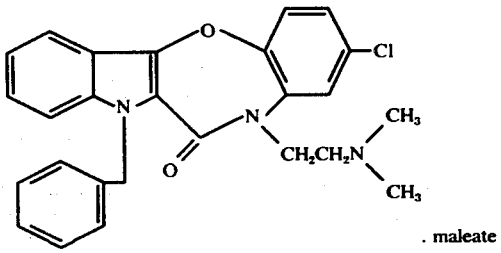

. maleate

7-BENZYL 3-CHLORO-5[2-(DIMETHYLAMINO)ETHYL]-7H-INDOLO 3,2-B][1,5]BENZOXAZEPINE-6(5H)-ONE MALEATE

In the same way as described in example 19, 3-chloro-7-benzyl-7H-indolo[3,2-b][1,5]benzoxazepine-6(5H)-one was alkylated with dimethylaminoethyl chloride. The crude-free base gave a crystalline salt on treatment with maleic acid in ethanol. Recrystallization from isopropanol gave analytical material, mp. 168°–70°.

Anal. Calcd. for $C_{26}H_{24}N_3O_2Cl.C_4H_4O_4$: C, 64.11; H, 5.02; N, 7.48; Cl, 6.31. Found: C, 63.98; H, 5.06; N, 7.34; Cl, 6.60.

EXAMPLE 23

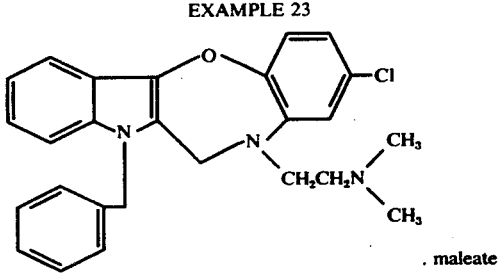

. maleate

7-BENZYL-3-CHLORO-5-[(2-DIMETHYLAMINO)ETHYL]-6,7-DIHYDRO-5H-INDOLO [3,2-B][1,5]BENZOXAZEPINE MALEATE

A solution of 7.8g of 7-benzyl-3-chloro-5[(2-dimethylamino)ethyl]-7-H-indolo[3,2-b][1,5]benzoxazepine-6(5H)-one in 100ml of ether was added dropwise to a suspension of 0.76g of lithium aluminum hydride in ether. The mixture was stirred for 18hours at ambient temperature, decomposed with saturated $NH_4Cl$ solution, and the alumina filtered and washed with ether. The ether solution was concentrated to a gum; the gum taken up in ethanol and treated with 2.0g of maleic acid. The crude salt was recrystallized from ethanol for analysis, mp. 149°–51°.

Anal. Calcd. for $C_{26}H_{26}N_3OCl.C_4H_4O_4$: C, 65.75; H, 5.52; N, 7.67; Cl, 6.47. Found: C, 64.10; H, 5.73; N, 7.20; Cl, 6.44.

EXAMPLE 24

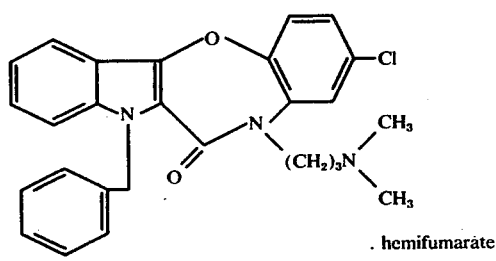

. hemifumarate

7-BENZYL-3-CHLORO-5-[(3-DIMETHYLAMINO)-PROPYL]-7H-INDOLO-[3,2-B][1,5]BENZOXAZEPINE-6(5H)-ONE HEMIFUMARATE

In the same way as described in example 19, 3-chloro-7-benzyl-7H-indolo[3,2-b][1,5] benzoxazepine-6(5H)-one was alkylated with 3-dimethylaminopropyl chloride. The crude base was treated with fumaric acid in ethanol and the salt recrystallized from methanol, mp. 203°–5°.

Anal. Calcd. for $C_{27}H_{26}N_3O_2Cl.½C_4H_4O_4$: C, 67.24; H, 5.45; N, 8.11; Cl, 6.84. Found: C, 67.25; H, 5.51; N, 7.93; Cl, 6.41.

EXAMPLE 25

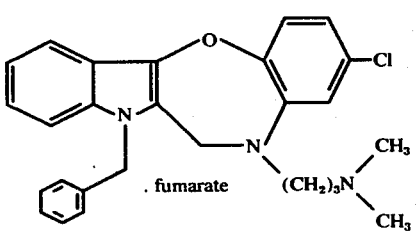

. fumarate

7-BENZYL-3-CHLORO-5-[3-(DIMETHYLAMINO)-PROPYL]-6,7-DIHYDRO-5H-INDOLO [3,2-B][1,5]BENZOXAZEPINE FUMARATE

In the same way as described in example 23, 7-benzyl-3-chloro-5-[(3-dimethylamino)propyl]-7H-indolo-[3,2-b][1,5]benzoxazepine-6(5H)-one was reduced. The crude base in ethanol was treated with fumaric acid and the salt recrystallized from ethanol, mp. 146°–7°.

Anal. Calcd. for $C_{27}H_{28}N_3OCl.C_4H_4O_4$: C, 66.25; H, 5.74; N, 7.48; Cl, 6.31. Found: C, 66.45; H, 5.84; N, 7.33; Cl, 6.39.

EXAMPLE 26

-continued

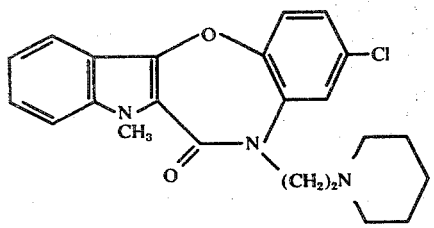

3-CHLORO-7-METHYL-5-(2-PIPERIDINOETHYL)-7-H-INDOLO-[3,2-b][1,5]BENZOXAZEPINE-6(5H)-ONE

In the same was as described in example 19, 3-chloro-7-methyl-7H-indolo[3,2-b][1,5]benzoxazepin-6(5H)-one was alkylated with piperidinoethyl chloride. The crude solid base was recrystallized from acetonitrile, mp. 160°–2°.

Anal. Calcd. for $C_{23}H_{24}N_3O_2Cl$: C, 67.39; H, 5.90; N, 10.25; Cl, 8.65. Found: C, 67.34; H, 5.94; N, 10.10 Cl, 8.56.

EXAMPLE 27

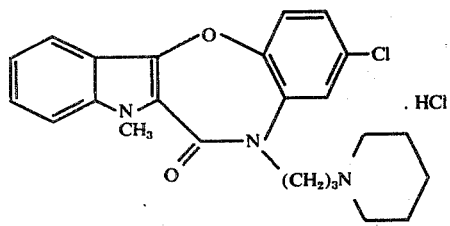

3-CHLORO-7-METHYL-5-(3-PIPERIDINO-PROPYL)-7H-INDOLO-[3,2-B][1,5]BENZOXAZEPIN-5(5H)-ONE HYDROCHLORIDE

In the same way as described in example 19, 3-chloro-7-methyl-7H-indolo-[3,2-b][1,5]benzoxazepin-6(5H)-one was alkylated with 3-chloropropyl piperidine, and the crude salt was recrystallized from isopropanol, mp. 202°–4°.

Anal. Calcd. for $C_{24}H_{26}N_3O_2Cl.HCl$: C, 62.61; H, 5.91; N, 9.13; Cl, 15.40. Found: C, 62.31; H, 5.98; N, 9.12; Cl, 15.37.

The compounds of this invention are CNS depressants and as such are useful as tranquillizers. Thus the compound of structure XI is active in blocking conditioned avoidance in rats at doses as low as 10 mg/kg. The compound of structure XII was a depressant

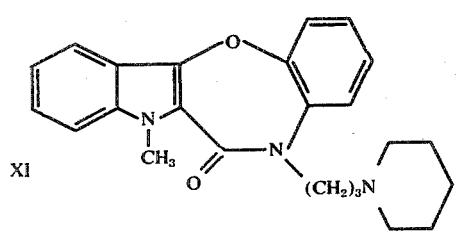

-continued

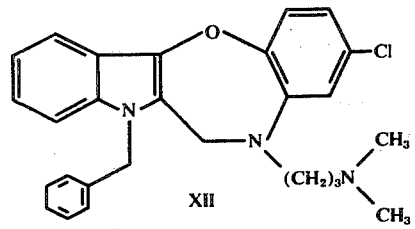

of motor activity in rats at 31 mg/kg.

I claim:

1. A substituted indolobenzoxazepine of the formula:

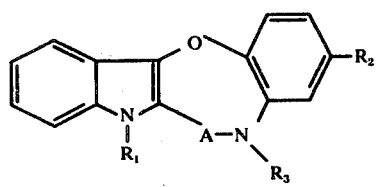

wherein $R_1$ is hydrogen, lower alkyl of 1 to 6 carbon atoms or an aralkyl group of 1 to 6 carbon atoms in the chain; $R_2$ is hydrogen, a halogen, lower alkyl of 1 to 6 carbon atoms or a trifluoromethyl group; A is a methylene group or a carbonyl group; $R_3$ is hydrogen, lower alkyl of 1 to 6 carbon atoms, or an ω-aminoalkyl group of the formula

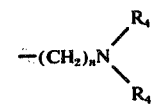

in which $n$ may be 2 to 4 and $R_4$ is hydrogen, lower alkyl of 1 to 6 carbon atoms or, taken together with the N atom form a heterocyclic ring of the formula

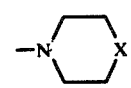

wherein X is oxygen, sulfur, —$CH_2CH_2$—, a bond connecting the adjacent carbon atoms, or $CH-R_5$ or $N-R_5$ wherein $R_5$ is hydrogen or lower alkyl of 1 to 6 carbon atoms.

2. A compound of the formula:

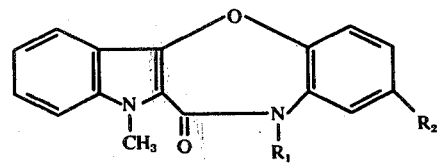

wherein $R_1$ is selected from the group consisting of

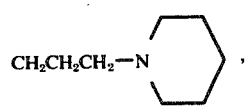

-continued

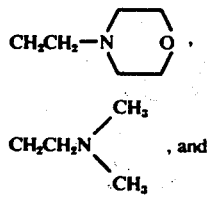

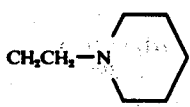

wherein R₂ is selected from the group consisting of —Cl, and

—H; and the hydrochloride salts thereof.

3. A compound according to claim 2 wherein R₁ is

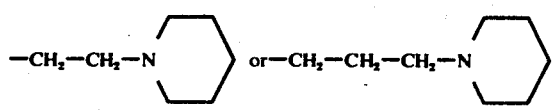

4. The compound according to claim 3 which is 7-methyl-5-(3-piperidinopropyl)-7H-indolo[3,2-b]-[3,2-b]-[1,5]benzoxazepin-6(5H)-one.

5. The compound according to claim 3 which is 3-chloro-7-methyl-5-[2-(1-piperidinyl)ethyl]-7H-indolo[3,2-b][1,5]benzoxazepin-6-(5H)-one.

6. The compound according to claim 3 which is 3-chloro-7-methyl-5-[3-(1-piperidinyl)propyl]-7H-indolo-[3,2-b][1,5]benzoxazepin-6-(5H)-one.

7. The compound according to claim 2 which is 5-[2-(dimethylamino)ethyl]-7-methyl-7H-indolo-[3,2-b[1,5]dibenzoxazepin-6(5H)-one.

8. The compound according to claim 2 which is 7-methyl-5-[2-(4-morpholinyl)ethyl]-7H-indolo[3,2-b][1,5]benzoxazepin-6(5H)-one.

9. A compound of the formula

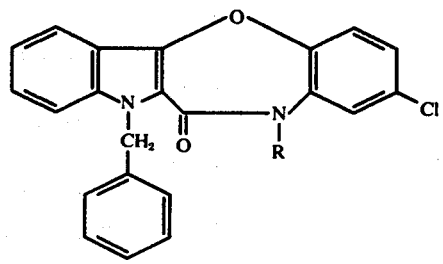

10. The compound according to claim 9 which is 3-chloro-5-[2-dimethyl amino)ethyl]-7-(phenylmethyl)-7-H-indolo[3,2-b][1,5]benzoxazepin-6(5H)-one.

11. The compound according to claim 9 which is 3-chloro-5-[3-(dimethylamino)propyl]-7-(phenylmethyl)-7H-indolo[3,2-b][1,5]benzoxazepin-6 (5H)-one.

12. A compound of the formula

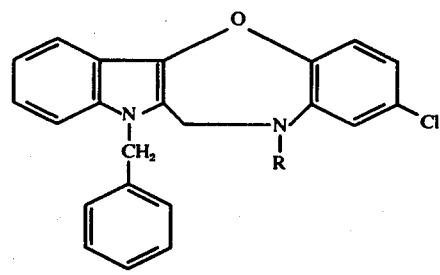

13. The compound according to claim 12 which is 3-chloro-6,7-dihydro-N,N-dimethyl-7-(phenylmethyl)-5H-indolo[3,2-b][1,5]benzoxazepine.

14. The compound according to claim 12 which is 3-chloro-5-[2-(dimethylamino)ethyl]-6,7-dihydro-7-(phenylmethyl)-5H-indolo[3,2-b][1,5] benzoxazepine.

15. 3-chloro-7-methyl-7H-indolo[3,2-b][1,5]benzoxazepin-6-(5H)-one.

* * * * *

UNITED STATES PATENT OFFICE
CERTIFICATE OF CORRECTION

PATENT NO. : 4,013,641
DATED : March 22, 1977
INVENTOR(S) : Richard E. Brown

It is certified that error appears in the above-identified patent and that said Letters Patent are hereby corrected as shown below:

Delete the assignee "Xerox Corporation, Stamford, Connecticut" and insert --- Warner-Lambert Company, Morris Plains, New Jersey ---.

Delete the attorneys "James J. Ralabate; James P. O'Sullivan; John E. Crowe' and insert --- Albert H. Graddis; Frank S. Chow; George M. Yahwak ---.

Signed and Sealed this twelfth Day of July 1977

[SEAL]

Attest:

RUTH C. MASON
Attesting Officer

C. MARSHALL DANN
Commissioner of Patents and Trademark